(12) United States Patent
Xu et al.

(10) Patent No.: US 8,936,815 B2
(45) Date of Patent: Jan. 20, 2015

(54) DEVICE FOR EXTERNAL USE IN ALTERNATIVE MEDICINE APPLICATIONS

(76) Inventors: Zhilong Xu, Toronto (CA); Mengjun Yang, Beijing (CN); Ping Li, Beijing (CN)

( * ) Notice: Subject to any disclaimer, the term of this patent is extended or adjusted under 35 U.S.C. 154(b) by 2036 days.

(21) Appl. No.: 11/377,858

(22) Filed: Mar. 17, 2006

(65) Prior Publication Data
US 2007/0098814 A1    May 3, 2007

(30) Foreign Application Priority Data

Nov. 3, 2005   (CN) .......................... 2005 1 0117269
Nov. 23, 2005  (CA) ...................................... 2529239

(51) Int. Cl.
| | |
|---|---|
| A61H 39/06 | (2006.01) |
| A61H 39/04 | (2006.01) |
| A61H 99/00 | (2006.01) |
| A61K 33/06 | (2006.01) |
| A61K 45/06 | (2006.01) |
| A61H 33/08 | (2006.01) |
| A61K 33/24 | (2006.01) |
| A61K 47/48 | (2006.01) |

(52) U.S. Cl.
CPC ................. *A61K 45/06* (2013.01); *A61K 33/06* (2013.01); *A61K 2300/00* (2013.01); *A61H 39/06* (2013.01); *A61H 39/04* (2013.01); *A61H 33/08* (2013.01); *A61K 33/24* (2013.01); *A61K 47/48992* (2013.01)
USPC ............ 424/682; 264/428; 264/429; 264/430

(58) Field of Classification Search
None
See application file for complete search history.

(56) References Cited

U.S. PATENT DOCUMENTS

| 5,238,627 A * | 8/1993 | Matsuhisa et al. ............ 264/645 |
| 6,641,776 B1 * | 11/2003 | Weaver et al. ................ 264/642 |
| 2003/0047027 A1 * | 3/2003 | Sato ................................ 75/228 |

FOREIGN PATENT DOCUMENTS

| JP | 2000007470 | | 1/2000 | |
| JP | 2000007470 A | * | 1/2000 | .............. C04B 41/87 |

OTHER PUBLICATIONS

JP2000007470_Translation.pdf. Machine translation of JP 2000007470 A (above). Obtained Nov. 24, 2008 from Japanese Patent Office website: http://dossier1.ipdl.inpit.go.jp/AIPN/odse__top_dn.ipdl?N0000=7400.*

* cited by examiner

*Primary Examiner* — Kevin S Orwig
(74) *Attorney, Agent, or Firm* — McMillan LLP

(57) ABSTRACT

The therapeutic device is an acupuncture device which is usable for treating chronic, but non-contagious diseases. The device is in the form of a solid chip or tablet having a unique composition, which can be placed on the body of a patient's acupuncture meridian points for the treatment. The treatment with this device is safe, more effective, non-invasive and easy to use over other alternative treatments because it does not involve the use of needles, medication, electricity and radiation.

2 Claims, No Drawings

DEVICE FOR EXTERNAL USE IN ALTERNATIVE MEDICINE APPLICATIONS

FIELD OF THE INVENTION

The invention relates to the field of alternative medicine, and more particularly to a non-invasive acupuncture replacement device.

BACKGROUND OF THE INVENTION

Chronic diseases plague people most, causing the significant deaths and medical costs. Chronic diseases can be attributed to miscellaneous origins that are often unidentified, resulting in ineffectiveness of a certain single biological-medicine healer, and leaving chronic diseases refractory. Chronic diseases require long-term, even lifetime, medication and/or therapy, often leading to toxicity and side effects due to overuse of medications. For instance, Vioxx, which is developed by Merck & Co. Inc. for treatment of arthritis, claims 60 thousand lives worldwide, outnumbering death toll of Americans in the Viet Nam War. Annually there are around one million people die of adverse events of medications in the world. In China, about 190 thousand people die of adverse events of drugs annually, ten times higher than that die of major infectious diseases (see Foreword for Prevention and Control of Adverse Events, 2002 edition, People's Medical Publishing House).

In an effort to eschew increasing adverse events of medications, some non-medication therapies known as Complementary and Alternative Medicines (CAM) have come into wide use in some developed nations. However, current CAM procedures have many pitfalls, including difficulty to be practiced, high cost, less evident in effectiveness and too painful to accept. Therefore, CAM requires new techniques and gadgets. In recent decades, gadgets of rehabilitative CAM have been springing up, outnumbering those intended for diagnosis (see China Medical Machines, 2001, volume 7, page 46).

Recently invented and used machines for treatment purpose are in general active ones, that is to say, electricity powered medical devices, falling into radiological therapy, microwave therapy, radiofrequency therapy, ultrasound therapy, laser therapy, millimeter wave therapy, infrared therapy, as well as other gadgets that apply sound, light, electricity, magnetic, mechanics and even medication. The machines and gadgets risk harmfulness to human body, including: electric shock, over-big output, energy distraction, explosion, fire danger, cease-function, abnormal performance, out of power, mechanic accident, malpractice, bacterial contamination, and interfering with other machines (see China Medical Machines, V01, 17 No 1). Passive medical machines are often non-invasive, free from using needle, electricity, electricity-mechanic parts and radioactivity. Medical machines that are non-invasive yet with evident rehabilitative effect on chronic diseases have not made debut so far.

SUMMARY OF THE INVENTION

This invention, Health Recovery Chip Kit, is a composite medical device, which consists of a chip, superficial fluid, effect membrane, an awl, bandage and cotton pick. It is intended to treat chronic diseases as a better alternative medicine.

The main component is the chip, which is made from Polar mineral tourmaline; Infrared material; Pliable magnetic material; Photo-catalytic material; Composite salt or oxide of rare earth; Calcium oxide; Adhesive material and an Inclusion compound. Manufacture of this chip is carried through nanometer handle processing. Adhesive material and inclusion compound are added prior to mould and thermal treatment.

This instrument is applicable to the rehabilitation treatment for a wide spectrum of chronic diseases. It is safe to human body and does no harm to ecology and environment. It has been approved to be more effective to the following treatments: Acupuncture and Moxibustion, Massage and Scrape therapy, cupping, medicine paste; Electrotherapy, Magnetism, infrared, physical therapy; Meditation, Chinese Qigong, and India yoga; Long-term Chinese herbal medicine and western medicine. Therefore, it can replace the above traditional treatments as better alternative.

DETAILED DESCRIPTION OF THE INVENTION

The detailed manufacturing and application methods of this invention, Health Recovery Chip (chips), are proved in this document. The kit is an effective device to replace the traditional alternative medical treatments, such as Acupuncture, Cupping and Therapeutic Message. The treatment is performed by applying the chips to various Acupuncture points for a period of less than 24 hours each time. It is non-invasive, safe, less labor intensive and environmental friendly. It has been used to treat chronic, but non-contagious diseases without needles, medication, electricity, Magnesium and radiation.

Manufacturing Methods and Procedures:

1. The method and processing of manufacturing the chips:
1.1 The raw material for making the chip consists of (by weight): (1) polar mineral tourmaline 20-40%; (2) infrared material 30-50%; (3) pliable magnetic material 5-10%; (4) the photo-catalytic material 1-5%; (5) composite salt or oxide of rare-earth 1-5%; (6) calcium oxide 5-10%; (7) adhesive material 2-5%; (8) an inclusion compound 1-5%.

1.2 Component selection:
1.2.1 The polar mineral tourmaline ore (beautiful jade) possess plentiful everlasting electrolytes and has more than ten kinds of silicate ores. This invention chooses one or more than one of tourmaline among Iron tourmaline, Magnesium tourmaline, Iron and Magnesium tourmaline, and Lithium tourmaline.

1.2.2 The infrared material should have distinct transmittances, refraction and chromatic dispersion in terms of the distinct wavelength of infrared rays. This invention chooses one or both of crystal sapphire alumina ($AL_2O_3$) and Magnesium oxide (MgO).

1.2.3 The pliable magnetic material can be magnetized repeatedly and demagnetized easily under the magnetic field. This invention chooses one or both of iron oxide (FeO) and iron trioxide ($Fe_2O_3$).

1.2.4 The photo-catalytic material (or nanometer powder), this invention chooses at least one among the Titanic oxide ($TiO_2$), Zinc oxide (ZnO), Tin oxide (SnO) and Tungsten oxide.

1.2.5 The composite salt or oxide of rare-earth is mixed material, this invention chooses one or more than one composite salt of rare-earth among $LaPO4$, $NdPO_4$, $Ce(NO_3)_3$ and $La(NO_3)$ either composite oxide of rare-earth among $CeO_2$, $Ce_2O_3$, $La_2O_3$ and $Nd_2O_3$.

1.2.6 Calcium oxide (CaO).

1.2.7 The adhesive material is one or more than one among Stearic Acid, Polyvinyl chloride, Pine resin, Flax oil and Castor oil.

1.2.8 The inclusion compound is one or more than one among Methyl Cellulose, Liquid Paraffin Wax, Colophon, and Polyvinyl Chloride.

1.3 The manufacture chips and technological processing:

1.3.1 The nanometer pellet processing and the thermal treatment: the polar mineral Tourmaline is routinely smashed into fine powder by either placing into the high energy ball mill to grind or to be pulverized through airflow millstone between 48 to 72 hours. Either process results in very small particles with crystalline grain diameter between 50-1000 nanometers. The thermal treatment will then be applied to tourmaline material with a range of temperature between 500-1000° C., which is about 2-3 hours. The same procedures also apply to the Infrared material. However, the photo-catalytic material can be processed similarly.

1.3.2 The proportion to fill a prescription and blend: According to the formulation of this invention, the proportion of eight materials to fill a prescription are: Polar mineral tourmaline nanometer powder 20-40%; Infrared material nanometer powder 30-50%; Pliable magnetic material 5-10%; The photo-catalytic material nanometer powder 1-5%; Composite salt or oxide of rare-earth 1-5%; Calcium oxide powder 5-10%; Adhesive material 2-5%; and an Inclusion compound 1-5%. Putting the eight listed materials into a grinding and blending machine to grind and blend. In order to blend sufficiently, the blending time is no less than 1 hour.

1.3.3 The pressing to form and sinter the chips: The blended material is placed into a mould plate according to predefined shapes. The pressure is 20-50 Mpa. After pressing, the formed chip is taken out of the mould plate and sintered by thermal treatment. The thermal treatment is performed at temperature between 500-1000° C. for a period of 2-3 hours. Then, the chip is left at room temperature for self-cooling between 48-72 hours and the chips are finalized.

1.4 The chips may have many different sizes, shapes and thicknesses. The common standard of mature chips in the clinical research has the diameter ≥25 mm and the thickness ≥3 mm.

2. Manufacture superficial fluid:

The method of this invention for making superficial fluid: submerging 1-3 of the finalized chips into 100 ml clean water for one hour, and then bottling the water. The chips have standard sizes and shapes with a diameter ≥25 mm and thickness ≥3 mm.

3. Manufacture the awl:

The method of this invention for making the awl: the mountain jade ore from Liaoning province of China is cut and polished into an awl shape. The awl has a base with a diameter of 0.6-0.8 cm, length of 7 cm, and a dull tip.

4. Manufacturing the membrane:

The method of this invention for manufacturing the membrane: The LLD-PEC low density string shaped polythene is mixed with corn oil to make a 0.18 mm thickness stretching membrane with heat and cold resistance at high temperature not exceeding 115° C. and low temperature not below −60° C. It is rolled and cut into 5 cm in width.

Standard Procedures and Methods of Using Health Recovery Chip Kit

1. Finding the therapeutic points on the skin of human body:

1.1 Acupuncture Points: according Chinese medicine and acupuncture theory.

1.2 Pressure points: the relevant corresponding skin point of the body reflecting the relevant internal organ with pathological changes.

1.3 Sensitive points: Using the awl to search the sensitive skin points you consider, which may vary in different pathological conditions.

2. Apply the chips on the point:

2.1 The superficial fluid can be applied either to the chips or to the skin points you selected, and then place the chips on the points.

2.2 Using the membrane to fix the chips to the skin points for 40-60 minutes. The membrane also enhances the therapeutic effect.

2.3 You can also use regular bandage or cotton band to keep the chips at appropriate points to keep moderate effectiveness. The difference between the enhancing membrane and regular bandage is that the membrane is more effective than bandage.

2.4 After 40-60 minutes, you can remove the chips from the points and clean up to finish one session.

2.5 The chip can also be imbedded under skin points of human body or internal organs for treatment of some chronic diseases.

This invention can apply the rehabilitation treatments of the most chronic diseases and not limited to the diseases below:

1. Chronic aches: Headache, Trigeminal pain, Coronary disc disease, Should pain, Waist strain, Lumbar pain, Coexistence of Cervical and Lumbar pain, Disc Disease, Rheumatoid arthritis, Gouty arthritis, Intercostal Neuralgia, Hucklebone nerve pain, Osteoporosis, Lumbar bone hyperplasia, Toothache, Vasculitis, Cancer.

2. Neurological and psychiatric diseases: Facial neuritis, Facial muscular convulsion, bell's palsy, Parkinson disease, Stroke (hemiplegia), Cerebrovascular Atherosclerosis, epilepsy, Dementia, Hysteria, Depression disease, Vertigo (Meniere's disease), Insomnia.

3. Respiratory diseases: Chronic bronchitis, Bronchus asthma, Bronchus Expansion (emptysis), Cold, Emphysema.

4. Digestive diseases: Chronic gastritis, Peptic ulcer, Midriff convulsion, Enteritis, Irritable Bowel Syndrome (IBS), Constipation, Chronic hepatitis, Fatty liver, Chronic cholecystitis, Gallstone.

5. Circulation system diseases: Hypertension, Hyperlipidemia, Coronary Heart Disease, Cardiac Arrhythmias, Cardiovascular Neurosis.

6. Urinary diseases: Chronic prostatitis, Prostate hyperplasia, Chronic Nephritis.

7. Diseases of orthopedics: Fracture, Dislocation of joint.

8. Disease of gynecology: Dysmenorrhea, Irregular menses, Inflammation of pelvic cavity, menopause, Infertility, Galactophore hyperplasia.

9. Diseases of andropathy: Impotence, Nocturnal emission, Prospermia, Infertility.

10. Diseases of facial features: Allergic rhinitis, Nasal sinusitis, Chronic Pharyngitis and tonsillitis, Tinnitus and deafness.

11. Diseases of ophthalmology: Cataract, Myopia, Hyperopia, Poor vision, Glaucoma, Dry eye, Trachoma, Eyes fatigue.

12. Endocrine and metabolic diseases: Hypothyroid disease, Diabetes.

13. Diseases of oncology: Anti-immunity tumor, Toxic and adverse effect of radiation treatment and chemotherapy.

14. Diseases of dermatology: General acne, Yellow speckle, Hives, Nervous dermatitis, Psoriasis disease, Strip anthema, Eczema.

15. Other diseases: idiopathic obesity, Obese breast, Chronic fatigue syndrome (suboptimal health), Air-conditioning related disease, Quit smoking, EX-Drug.

Test Results

This invention offers a new technology for rehabilitation of chronic diseases called surface therapy technology, which can play a versatile role mimicking acupuncture and moxibustion, massage, manipulation, scraping, fire cup, herbal plaster, electricity therapy, magnetic therapy, infrared therapy, far infrared therapy, herbal remedies, Chinese Qigong, India Yoga. It can also relieve people from exhausting long-term chemotherapy. It is highly effective for rehabilitating chronic diseases.

The inventors, together with physician Liu Yu, applied this health recovery chips to 590 patients that are plagued by 21 kinds of chronic diseases in 6 health club of China Health Way Campaign. Among the 590 patients, 276 were men and 314 were women. The youngest was 8 years old and the oldest was 85. The longest therapeutic course lasted 35 days and the shortest course was in one day. Diseases that were treated with the rehabilitation chip involved 21 kinds of maladies: headache, chronic rhinitis, coronary diseases, hypertension, arteriosclerotic brain disease, premature beat, slipped disk, cervical hyperosteogeny, gonitis, scapulohumeral periarthritis, gout, acute lumbar sprain, cyclomastopathy, insomnia, infection in upper respiratory tract, chronic bronchitis, facial palsy, eczema, acute urinary tract infection, acute gastro-enteritis and toothache.

Out come of treatment with health recovery chips unit:

Treatment was successful in up to 91 patients, falling into followings: 1. Headache: 12 patients. (Acupuncture Points: Yintang, Fengchi, Yongquan, Hegu, Neiguan, TaiYang, Ashixue); 2.

Infection in upper respiratory tract: 15 patients (Acupuncture Points: Dazhui, Waiguan, Lieque, Quchi); 3. Chronic bronchitis 4 (Acupuncture Points: Yingxiang, Yintang, Hegu, Lieque, Zusanli, Feishu); 4. Gout: 2 patients (Acupuncture Points: SanYinjiao, Taixi, Zusanli, Ganshu, Shenshu, Ashixue); 5. Toothache: 10 patients (Acupuncture Points: Xiaguan, Jiache, Fengchi, TaiYang, Ashixue); 6. Gonitis: 5 patients (Acupuncture Points: Heding, Dubi, Qiyan, Yinlingquan, Zusanli, Weizhong, Ashixue); 7. Insomnia: 5 patients (Acupuncture Points: Dazhui, Anmian, Fengchi, Neiguan); 8. Eczema: 1 patient (Acupuncture Points: Quchi, Neiguan, Xuehai, Fengshi, Zusanli, SanYinjiao); 9. Acute gastro-enteritis: 6 patients (Acupuncture Points: Shangwan, Zhongwan, Zusanli, 4 Acupuncture Points around navel, Ashixue); 10. Acute lumbar sprain: 1 patient (Acupuncture Points: Shenshu, Weizhong, SanYinjiao, Ashixue); 11. Chronic bronchitis: 3 patients (Acupuncture Points: Dazhui, Tiantu, RenYing, Feishu, Neiguan, Dingchuan, Shanzhong, Zusanli, Chize); 12. Scapulohumeral periarthritis: 5 patients (Acupuncture Points: Rushu, Jianjing, Jianliao, Jianyu); 13. Cyclomastopathy: 1 patient (Acupuncture Points: Shanzhong, Rugen, Wuyi, Ganshu, Pishu, SanYinjiao); 14. Facial palsy: 1 patient (Acupuncture Points: Dazhui, TaiYang, Sibai, Shangguan, Xiaguan, Dicang, Jiache, Juliao); 15. Ischialgia: 20 patients (Acupuncture Points: Shenshu, Baihuanshu, Zhibian, Huantiao, Chengfu, Yinmen, Weizhong, SanYinjiao).

Up to 455 patients showed some certain effectiveness, and 20 patients did not remit their diseases. (Mostly were due to situations that were too severe or were unable to persist in the therapy for some reason).

Another trial that was conducted in previous two months on 590 patients, who were members of six clubs of Way to Health Campaign, showed that the successful treatment rate was 16%, effectiveness rate was 77% and total effectiveness rate was 93%.

This rehabilitation chip is also used in many hospitals of China in an effort to treat chronic diseases. The followings are about detailed information about the trials in the hospitals:

I. The inventor cooperated with physicians of Guangdong Shanwei Hospital for Traditional Chinese Medicine in his effort to treat dizziness with the chips. The therapeutic effect is satisfactory.

1. About clinical data:

Of the 54 patients, 24 were outpatients and 30 were inpatients. 21 were men and 33 were women. The youngest patient was 17 years old and the oldest was 87. The average age was 50. The shortest disease course was 0.5 day and the longest was 21 years, the average time was 2.2 years. 25 patients were suffering brain arteriosclerosis, 10 were suffering hypertension, 8 were suffering cervical spondylopathy, 14 were suffering Meniere's syndrome, 2 were suffering climacteric syndrome, 3 were suffering hyper viscosity syndrome, 2 were suffering neurasthenia, 1 was victim of brain trauma residue, 2 were suffering chronic alcoholism. All of the 54 patients had principal symptom of dizziness.

2. About treatment:

All 54 patients underwent treatment with rehabilitation chips

Master points: Baihui, TaiYang, Neiguan, Zusanli.

Accessory points: add Taixi and Shenshu in case of deficiency in kidney Yin; add Geshu and Pishu in case of deficiency in Qi and blood; add Fenglong and Pishu in case of stagnation of phlegm-dampness; add Taichong and Fengchi in case of Excess of Liver Yang.

Procedure: apply the chip onto master Acupuncture Points and match them with accessory Acupuncture Points according to syndrome differentiation. Dip a cotton stick into surface liquid and moisten the contact area on the skin, apply the chip onto the Acupuncture Points and immobilize it with poromeric adhesive tape. Retain the chip on Acupuncture Points for one hour each session of therapy.

3. Outcomes of treatment:

Of the 54 patients, 43 were clinically treated (The patient's symptom disappeared utterly, being able to return normal life); 38 patients remitted their symptoms (The patient's symptom was obviously alleviate); 2 patients showed no effect (symptoms maintained as usual). Total effective rate was 96.2% and average duration for being treated was 18 days.

In addition to the preceding maladies, the inventor also put this chip into treatment of 50 patients with stroke in cooperation with physicians of Guangdong Shanwei Hospital for Traditional Chinese Medicine. The therapeutic effect is convincing.

1. About clinical data:

Of the 50 patients, 38 were men and 12 were women. The youngest patient was 33 years old and the oldest was 76. 46 patients had a disease course shorter than 3 months and 4 longer than 3 months. 30 were suffering sanguineous apoplexy and 20 were suffering cerebral embolism.

2. About treatment:

2.1 Master Acupuncture Points: Shuigou, Neiguan, Laogong, Quchi, Weizhong. Add Jianyu, Hegu, Waiguan, Huantiao, Yanglingquan, Zusanli, Jiexi, Kunlun, Taichong in case of hemiparalysis Add Dicang or Jiache, Hegu, Neiting, ChengQi, Yangbai, Cuanzhu, Kunlun, Yanglao in case of facial hemiparalysis; add Lianquan, Tongli, Yamen, Fengfu, Tiantu, and SanYinjiao in case of slurring of speech.

2.2 Procedures: apply the chip onto master Acupuncture Points and match them with accessory Acupuncture Points according to syndrome differentiation. Dip a cotton stick into surface liquid and moisten the contact area on the skin, apply the chip onto the Acupuncture Points and immobilize it with poromeric adhesive tape. Retain the chip on Acupuncture Points for one hour each session of therapy. Each session of therapy uses 4-5 Acupuncture Points and alternates the Acupuncture Points. Once daily and ten sessions make up one therapeutic course. A two-day interval is needed before administering next therapy.

3. Criteria for determining effectiveness:

Cure: speak articulately; walk without need of support, able to rise up upper limb and grab an article, lead a life without nursing care, and have feelings everything is ok.

Obvious effectiveness: able to speak relatively articulately, walk with need of support, able to grab an article but feel frail in fist, lead a life with little nursing care and limbs occasionally feel discomfort.

Some certain effectiveness: unable to speak articulately but can be expressed, have some improvement in myodynamia of extremities but have poor rehabilitation in functions, leading a life with nursing care. No effect: maintain symptoms and signs after therapy.

4. Outcomes of the therapy with those chips:

17 (34%) patients were treated; 16 (32%) patients showed obvious effectiveness, 12(24%) patients showed some certain effectiveness, 5 (10%) patients showed no effect. Total effectiveness rate was 90%. At least one therapeutic course was conducted and the longest was 9 therapeutic courses. The average was 3.8 therapeutic courses.

For relationship between disease and effectiveness of the chip, see table 1. For relationship between disease course and effectiveness of the chip, see table 2.

TABLE 1

Relationship between disease and effectiveness of the chip

|  | Patients number | Cure (%) | Obvious effectiveness(%) | Some certain effectiveness(%) | No effect(%) |
|---|---|---|---|---|---|
| Sanguineous apoplexy | 30 | 10 (35) | 12 (40) | 6 (18.33) | 2 (6.67) |
| Cerebral embolism | 20 | 6 (31.5) | 4 (20) | 7 (33.5) | 3 (15) |

TABLE 2

Relationship between disease course and effectiveness of the chip

| Disease course | Patients number | Cure | Obvious effectiveness | Some certain effectiveness | No effect |
|---|---|---|---|---|---|
| 1-3 months | 46 | 15 | 15 | 12 | 4 |
| Longer than 3 months | 4 | 1 | 2 | 1 |  |

II. The inventor cooperated with physicians of People's Hospital of Shimen County in his effort to treat constipation-type irritable bowel syndrome with the chip. The therapeutic effect is satisfactory.

1. Data and Treatment:

1.1 About clinical data:

During October 2004-June 2005, 50 patients with irritable bowel syndrome who attended the digestive sector of the hospital were treated with the chips. All patients underwent lab test, barium meal examination and colonoscopy in order to exclude presence of organic changes in either intestinal or entire body that can lead to constipation. All patients met criteria set by 1998' Rome Convention. 18 were men, 32 were women. The oldest was 63 years old, the youngest was 15, and the average age was 37. The longest disease course was 20 years and the shortest was half a year, the average disease course was 5 years.

1.2 The patients were treated according to syndrome differentiation:

The patients fell into two types: stagnation of the liver-Qi and deficiency in both heart and spleen. Stagnation of the liver-Qi: dry or less dry feces, difficult evacuation, infrequent evacuation less than 3 times each week or even worse have bowel movement once each week. Abdominal flatulence and pain involves flanks, bitter taste, dizziness, and symptoms fluctuate with mood. The tongue texture is pale and the coating is thin white, and the pulse is fine and weak. Among 50 patients, 21 met criteria for stagnation of the liver-Qi, accounting for 42% and 29 met criteria for deficiency in both heart and spleen, accounting for 58%.

1.3 About treatment:

All patients underwent psychological counseling helping them get relieved from anxiety and depression, dietary adjustment helping them to take more plant fibers. They are also informed of rational habits of feces evacuation as having bowel movement at a certain time, do not smoke or read during bowel movement. All medications either chemical or herbal were stopped. On the basis of the preceding activities, the patients received treatment with rehabilitation chip according to syndrome differentiation.

The master Acupuncture Points were bilateral Dachangshu, Zusanli and Zhongwan. For stagnation of the liver-Qi, add bilateral Yanglingquan and Xiangjian with a dispelling maneuver (Xiefa). For deficiency in both heart and spleen, add bilateral SanYinjiao and Guanyuan. Dip a cotton stick into surface liquid and moisten the contact area on the skin, apply the chip onto the Acupuncture Points and immobilize it with adhesive tape. Retain the chip on Acupuncture Points for one hour each session of therapy. Once daily and ten days make up one therapeutic course. A two-day interval is needed before every two sessions. One episode of observation lasted two months.

2. Criteria for determining effectiveness and results:

2.1 Criteria for determining effectiveness:

Obvious effectiveness: symptoms disappear; restore normal bowel movement without relapse within two months.

Some certain effectiveness: symptoms are strikingly alleviated; restore relatively normal bowel movement without relapse within two months.

No effect: maintain unchanged after therapy or have to resort to medication therapy.

2.2 Results Among 50 patients with stagnation of the liver-Qi, 15 patients showed obvious effectiveness, 4 patients showed some certain effectiveness, 2 patients showed no effect. Among 16 patients with deficiency in both heart and spleen, 16 showed obvious effectiveness, 9 showed some certain effectiveness, and 4 showed no effect. Regardless of syndrome differentiation, overall rate of obvious effectiveness was 61% (31 patients), rate of no effect was 12% (6 patients), and general effectiveness rate was 88%.

III. The inventor also cooperated with physicians of No. 2 Hospital for Traditional Chinese Medicine of Changde City in his effort to treat hypertension with the chips.

1. About clinical data:

Among 66 patients, 41 were men, 35 were women. One patient was younger than 45, 22 were between 45 and 55 years old, and 42 were older than 55. The shortest disease course was half year and the longest was 9 years. Criteria for classify Ying hypertension were set by 1978' national conference on cardiovascular diseases and WHO as well. 12 patients were in stage I, 47 patients were in stage II and 7 patients were in stage III.

2. About treatment:

2.1 Acupuncture Points applied: Dazhui, Neiguan, Jiangyaxue, Taichong, Hegu, Fengchi (all were bilateral), Ganshu and Baihui.

2.2 Procedures: Dip a cotton stick into surface liquid and moisten the contact area on the skin, apply the chip onto the Acupuncture Points and immobilize it with poromeric adhesive tape. Retain the chip on Acupuncture Points for one hour each session of therapy. Each session of therapy uses 4-5 Acupuncture Points and alternates the Acupuncture Points. Once daily and ten sessions make up one therapeutic course. During the therapy, refrain from smoking and alcohol and fretfulness, keep urine and feces evacuated, and stop any other therapies.

3. Criteria for determining effectiveness and outcomes of the therapy:

Posterior to treatment of 66 patients for half a year, 47 were treated: headache and dizziness disappeared, blood pressure returned to normal level, did not relapse within half a year on follow-up; 18 patients showed obvious effectiveness: headache and dizziness disappeared, blood pressure returned to normal level, but relapsed within half a year on follow-up; 6 patients showed some certain effectiveness: headache and dizziness remitted, but blood pressure fluctuated between normal level and outpoint; 5 patients showed no effect: blood pressure did not return to normal level or failed to restore normal range even occasionally symptoms remitted. General effectiveness rate was 92%, and cure rate was 71%.

IV. The inventor cooperated with physicians of No. 1 Hospital for Traditional Chinese Medicine of Changde City in his effort to treat coronary disease with the chips.

1. About clinical data:

Among 50 patients, 37 were men, 13 were women. The oldest was 76 years old; the youngest was 23. 8 patients were between 40-49 years old, 20 were between 50-59, 16 were between 60-69, 3 were between 70-79. According to criteria set by western medicine, 17 patients were suffering angina pectoris, including 16 with stable angina pectoris, one with unstable angina pectoris; 15 were suffering arrhythmia, including 10 patients with ventricular premature beat, 2 with arterial premature beat, one with sick sinus syndrome, one with arterial fibrillation, one with complete right bundle block; 9 were suffering myocardial infarct, and 11 were with remote myocardial infarction. According to criteria set by traditional Chinese medicine, 13 belonged to blood stasis, 11 belonged to obstruction by phlegm, 8 belonged to stagnation of Qi, 7 belonged to deficiency in heart-Qi, 11 belonged to deficiency in both Qi and Yin, and 5 belonged to deficiency in heart-Yang.

2. About treatment:

2.1 Acupuncture Points applied: Acupuncture Points were principally from heart and pericardium channel, matched with Acupuncture Points that were crisscross of eight channels as well as the Xi-points that belong to heart and pericardium. First group: Juque, Xinshu, Geshu, Neiguan, Gongsun and Yinxi; second group: Shanzhong, JueYinshu, SanYinjiao and Ximen. Alternate the two groups: Add Taiyuan in case of obstruction by Phlegm; add Shanzhong or Geshu in case of asthenia cold.

2.2 Procedures: Dip a cotton stick into surface liquid and moisten the contact area on the skin, apply the chip onto the Acupuncture Points and immobilize it with poromeric adhesive tape. Retain the chip on Acupuncture Points for one hour each session of therapy. Once daily and ten sessions make up one therapeutic course. An observation session consisted of 3 therapeutic courses.

2.3. Criteria for determining effectiveness:

2.3.1 Criteria for determining effectiveness over treating angina pectoris and illustrated by ECG: 1979' national Criteria for Evaluating Effectiveness over Treating Angina Pectoris and Illustrated by ECG.

2.3.2 Criteria for determining effectiveness over main symptoms (choked pain, palpitation and short breath): obvious effectiveness: symptoms disappear utterly or almost utterly; alleviated: symptoms become obviously alleviated; no effect: symptoms remain unchanged after therapy; deteriorated: symptoms become deteriorated after therapy.

2.3.3 Criteria for determining effectiveness is over index of blood fat according to 1974/Shanghai Panel for Cooperation on study of red sage root compound.

3. Results:

3.1 Effectiveness over main symptoms (see Table 1)

3.2 Effectiveness over syndrome differentiation of TCM (see Table 2)

3.3 Effectiveness over index of blood fat: there were 30 patients who had over high cholesterol and 23 of them showed effectiveness; there were 20 patients had over high TG and 10 of them showed effectiveness.

TABLE 1

Effectiveness over main symptoms

| Main symptoms | Number of patient | obvious effectiveness | Alleviated | No effect | Deteriorated | Effectiveness rate(%) |
|---|---|---|---|---|---|---|
| Chest pain | 30 | 20 | 6 | 2 | 2 | 86.66 |
| Choked chest | 32 | 12 | 16 | 4 | 0 | 87.50 |
| Palpitation | 23 | 10 | 8 | 5 | 0 | 78 |
| Short breath | 13 | 5 | 7 | 1 | 0 | 92 |

TABLE 2

Effectiveness over syndrome differentiation of TCM

| Main symptoms | Number of patient | Obvious effectiveness | Alleviated | No effect |
|---|---|---|---|---|
| blood stasis | 13 | 8 | 4 | 1 |
| Obstruction by phlegm | 11 | 5 | 5 | 1 |
| Stagnation of Qi | 8 | 2 | 4 | 2 |
| Deficiency in heart-Qi | 7 | 3 | 3 | 1 |
| Deficiency in both Qi and Yin | 6 | 3 | 2 | 1 |
| Deficiency in heart-Yang. | 5 | 2 | 2 | 1 |

3.4 Effectiveness over changes on ECG: all disorders on ECG were alleviated, including ST-T alterations, V-wave alteration, atria fibrillation, sick sinus syndrome, frequent ventricular premature beat, frequent atria premature, and complete right bundle block.

3.5 Effectiveness over cardiac function: all disorders in cardiac function were alleviated, with LVET elongate, PEP and TICT shortened, and PEP/LVET dropped.

V. The inventor cooperated with physicians Meili and Liu Guang in their efforts to treat senile dementia with the chips.

1. About clinical data:

Among 76 patients, 46 were men and 30 were women. They aged between 59 to 78 and average of 73. Their disease courses lasted 9 months to 8 years, with an average of two years and eight months.

2. About Treatment:

Acupuncture Points: Baihui, Sishencong, Dazhui, Guanyuan.

Procedures: Dip a cotton stick into surface liquid and moisten the contact area on the skin, apply the chip onto the Acupuncture Points and immobilize it with adhesive tape. Retain the chip on Acupuncture Points for one hour each session of therapy. Once daily and ten sessions make up one therapeutic course. A two-day interval is needed before administering next therapy. A usual duration of therapy was 2-3 months. Patients were allowed to use other medications during using this chip therapy, including hypertension relieving pills, fat-reducing medications, sugar-reducing medications and medications that inhibited agglomeration of blood platelet.

3. Results:

Criteria for determining effectiveness

Cure: symptoms disappear, lead a life without nursing care, and restore normal social activities;

Obvious effectiveness: symptoms become alleviated, but still suffere retardation in reaction, intelligence, unable to lead a life without nursing care;

No effect: remain unchanged in symptoms and signs after therapy.

4. Outcomes of therapy:

7 patients were treated, 33 showed obvious effectiveness; 26 patients showed some certain effectiveness; 10 patients showed no effect. Of those 19 patients who had disease course shorter than one year, 6 were treated, 9 showed obvious effectiveness. All patients that showed no effect had a disease course longer than 3 years. The effectiveness rate was 86%.

VI. The inventor cooperated with physician Tang Guanghua in his effort to treat chronic enteritis with the chips.

1. About clinical data:

Among 64 patients, 38 were men, 26 were women. 8 patients were between 30-40 years old, 18 were between 41-50, 26 were between 51-60, and 12 were older than 61. The shortest disease course was one year and the longest was 12 years. Criteria for confirming chronic enteritis: (1) History of acute enteritis or recurrence of enteritis; (2) Upon onset of enteritis, patients suffered from diarrhea and abdominal pain, accompanied by chronic malnutrition and abdominal tenderness. Routine stool test showed white blood cells and few pyocytes. (3) Being excluded from other non-specific enteritis using X-ray barium meal examination and colonoscopy.

2. About treatment:

2.1 Acupuncture Points applied: four Acupuncture Points around navel, Zhongwan, Tianshu, Guanyuan, Zusanli, Shangjuxu, Shenshu, Pishu, Dachangshu, Quchi, SanYinjiao.

2.2 Procedures: The preceding Acupuncture Points fell into two groups: first group: four Acupuncture Points around navel, Zhongwan, Tianshu, Guanyuan, Zusanli, Shangjuxu, Hegu and SanYinjiao. Second group: Pishu, Shenshu, Dachangshu, Zusanli, Shangjuxu, Hegu. Alternate the two groups upon using. Dip a cotton stick into surface liquid and moisten the contact area on the skin, apply the chip onto the Acupuncture Points and immobilize it with poromeric adhesive tape. Retain the chip on Acupuncture Points for one hour each session of therapy. Use 4-5 Acupuncture Points each session. Ten sessions make up one therapeutic course.

3. Results of treatment:

Criteria for determining effectiveness

Cure: stool restores normal shape, being evacuated once daily. Alleviated: stool restores normal shape, being evacuated twice daily; no effect: stool remains unchanged.

Among 64 patients, 31 patients were treated, accounting for 48.4%; 28 patients were alleviated, accounting for 43.7%; 5 patients showed no effect, accounting for 7.9%; General effectiveness rate was 92.1%.

VII. The inventor cooperated with physicians of People's Hospital of Tianjin City in his effort to treat 68 patients with chronic Prostatitis with the chips.

1. About clinical data:

All 68 patients were attendants to the hospital during June 2004 to June 2005, most of them had undergone treatment using either chemical or herbal medications. The youngest patient was 17 years old and the oldest was 76. 3 patients were younger than 20. 5 patients were between 21-30 years old, 8 were between 31-40, 17 were between 41-50, and 35 patients were older than 50. The shortest disease course was half a year and the longest was 20 years. 57 patients were married, 11 were unmarried. Main complaints included sore and swelling pain in back and bottom, bearing down pain in lower abdomen and perineum, frequent urination, difficult urination, dripping urination. 6 patients were complicated with severe nervosism and sexual disorder. Examination of prostatic fluid under microscopy: 28 patients showed white blood cells (+), 21 patients showed white blood cells (+ +), 15 patients showed white blood cells (+ + +), 4 patients showed white blood cells (+ + + +). 32 patients had prostatomegaly, and 2 patients had calculus of prostate.

2. About treatment:

2.1 Acupoint: Master Acupuncture Points: Xiaochangshu, Pangguangshu, Pishu, Ciliao, Guanyuan, Zhongji. Accessory Acupuncture Points: Yinlingquan, SanYinjiao, Taixi. For excess of viscera, add Qugu, Waigua; for deficiency of viscera, add Shenshu, Zusanli.

2.2 Procedures: Dip a cotton stick into surface liquid and moisten the contact area on the skin, apply the chip onto the Acupuncture Points and immobilize it with poromeric adhesive tape. Retain the chip on Acupuncture Points for one hour each session of therapy.

Each session of therapy uses 4-5 Acupuncture Points and alternates the Acupuncture Points. Once daily and ten sessions make up one therapeutic course. A 3-5 days interval is needed before administering next therapy. In case both Acupuncture Points and Mu (collecting) points are used, put the needle prone position first and supine position second. For more frequently only one position is used upon each session.

3. Observations of effectiveness:

3.1 Criteria for determining effectiveness:

Cure: self-felt symptoms disappear, restore normal examination of prostatic fluid under microscopy;

Obvious effectiveness: symptoms disappear, less than 3 WBC/HP are found; alleviated: symptoms become alleviated obviously, 4-6 WBC/HP are found; No effect: symptoms and findings under microscopy remain unchanged.

3.2 Outcome of therapy: Posterior to 2-3 therapeutic courses, 18 patients were treated, accounting for 26.5%; 21 patients showed obvious effectiveness, accounting for 30.9%; 22 patients alleviate their symptoms, accounting for 32.3%; 7 patients showed no effect, accounting for 10.3%. General effectiveness rate was 89.7%. For effectiveness varying with age segments, see Table 1

TABLE 1

Effectiveness varying with age segments

| Age (Years) | Number of patient | Cure | Obvious effectiveness | Alleviated | No effect | Effectiveness rate (%) |
|---|---|---|---|---|---|---|
| 17-20 | 3 | 1 | 2 | — | — | — |
| 21-30 | 5 | 3 | 1 | 1 | — | — |
| 31-40 | 8 | 4 | 2 | 2 | — | — |
| 41-50 | 17 | 6 | 7 | 3 | 1 | 94.1 |
| 50-76 | 35 | 4 | 9 | 16 | 6 | 82.9 |

VIII. The inventor cooperated with physicians of NO. 1 affiliated Hospital of GuiYang College for Traditional Chinese Medicine in his effort to treat chronic nephritis and nephrosis with the chips.

1. About clinical data:

52 patients were randomized into group treated with the chip and the other 47 patients into group treated with medication as control. CGN fell into ordinary type, manifesting slow onset, protracted disease course, having little or much proteinuria, hematuria, cylindruria, edema, hypertension, and renal failure; hypertension type, besides preceding findings, this type is striking for very high blood pressure; type of flare in course of chronic plaguing: manifesting features of acute nephritis in course of chronic plaguing. NS was always accompanied by large amount of proteinuria (≥3.5 g/24 h), hypoproteinemia (serum albumin<30 g/L), hyperlipemia and explicit edema. All patients were classified into certain types according to 1985 national conference on diseases of glomerulus (Nanjing). Some underwent renal biopsy for pathological classification. Group treated with rehabilitation chips included: 20 patients with ordinary type of CGN, 12 patients with type of flare in course of chronic plaguing, 5 patients with striking hypertension. Group treated with medication as control included: 18 patients with ordinary type of CGN; 12 patients with type of flare in course of chronic plaguing, 4 patients with striking hypertension, and 13 patients with NS.

2. About treatment:

Group treated with rehabilitation chips: Shenshu, Pangguangshu, Sanjiaoshu, Guanyuan, Qihai, SanYinjiao, Shuitong, Shenjue, HuiYin, Qugu. Procedures: Dip a cotton stick into surface liquid and moisten the contact area on the skin, apply the chip onto the Acupuncture Points and immobilize it with poromeric adhesive tape. Retain the chip on Acupuncture Points for one hour each session of therapy. Each session of therapy uses 4-5 Acupuncture Points and alternates the Acupuncture Points. Once daily and ten sessions make up one therapeutic course. Patients in this group were also administered routine treatment, that is to say, inosine 0.2 g, three times daily, Liuweidihuang concoction (add or remove some constituents in case of need), use dihydrochlorothiazide to treat edema and remove retention of water, use nifepine and captopril to relieve hypertension. The control group only received the routine treatment.

3. Criteria for effectiveness:

3.1 Parameters for observing effectiveness: routine urine test, quantitative measurement of protein in 24 h urine, $\beta 2\beta$-MG, urine $\beta 2$-MG, blood routine test, blood creatinine, blood urea nitrogen, complement, Ig and renogram.

3.2 Criteria for determining effectiveness: Posterior to therapy, findings of followings indicate effective and based on which effectiveness rate was calculated: observational measurement of urinary protein was negative, quantitative measurement of protein in 24 h urine was ≤150 mg, normal renal function, and normal immunity test. Lowering of blood pressure, decreasing of urine protein and improvement of renal function were not discussed in determining effectiveness.

4. Outcome of therapy:

Posterior to 1-3 therapeutic courses using rehabilitation chip, protein disappeared in urine of 39(75%) patients. 17 out of 20 patients with ordinary type CGN showed effectiveness, 9 out of 12 patients with type of flare in course of chronic plaguing showed effectiveness, one out of 5 patients with striking hypertension showed effectiveness, 12 out of 15 patients with NS showed effectiveness. As for the control group, protein disappeared in urine of 16 (34%) patients. 4 out of 18 patients with ordinary type CGN showed effectiveness, 4 out of 12 patients with type of flare in course of chronic plaguing showed effectiveness, none of 4 patients with striking hypertension showed effectiveness, 8 out of 13 patients with NS showed effectiveness. Biopsy of patients treated with chip showed they mostly featured minute lesions, mild proliferation of mesenteric tissue, and membranate nephrosis. All patients showed effectiveness had normal value of Cr, Bun, C3 and renogram showed favorable profile. Most patients came through.

Effectiveness rate between the two groups differed significantly ($u>2.58$, $P<0.05$), indicating group treated with chip plus medication was superior to group treated with only medication. Due to scarcity of patients undergone biopsy, relationship between pathological type and effectiveness was unable to obtain. However, aftermath of protein in urine was related to pathological classification.

IX. The inventor cooperated with physicians of Linli Hospital for Traditional Chinese Medicine in his effort to treat 56 patients with trigeminal neuralgia with the chips.

1. About clinical data:

56 patients with trigeminal neuralgia were treated. 20 were men, 36 were women. The oldest was 78 years old; the youngest was 35.5 patients suffered pain in first branch, 15 in second branches and 16 in third branches. 20 were compounded. The shortest disease course was one month and the longest was 10 years. 48 patients were primary and 8 were secondary. 3 suffered cholesteatoma; 5 suffered eye-branch residual pain due to infection of herpes zoster virus.

2. About treatment:

For first branch: Yuyao and Xiaguan were master Acupuncture Points, matched with Yangbai, Shangxing, Hegu, Neiting. For second and third branches: Sibai, Xiaguan, Dicang, Jiachengjiang, Hegu, Neiting. For lesion on head and face, Acupuncture Points on pained side were used. And Hegu and Neiting were used bilaterally. Once daily, ten sessions make up one therapeutic course. The patients rest for 3-5 days before administering next therapeutic course.

3. Criteria for effectiveness:

Clinical treated: pain on face utterly disappears.

Obvious effectiveness: pain on face becomes dramatically infrequent.

Alleviated: pain on face became alleviated and infrequent.

No effect: pain on face remains unchanged in severity and frequency after the therapy.

4. Outcome of therapy:

38 patients had orally taken carbamazepine and stopped it for poor effect. They refrained from carbamazepine during therapeutic course with the chip. 18 patients who had not taken carbamazepine were administered carbamazepine 0.1 g bid during their therapeutic course with the chip. The least sessions for using the chip were 6 times and the most were 20 times. 42 were clinically treated, accounting for 75%; 9 patients showed obvious effectiveness, accounting for 16.1%; 5 patients alleviated, accounting for 8.9%; none of the chip-treated showed no effect; general effectiveness rate was 100%. 42 patients did not relapse within half a year follows, 11 patients relapsed within 3-4 months, however with mild symptoms, and symptoms disappeared for another 5-10 session therapy with the chip. 3 patients with cholesteatoma were referred to other hospital for operation, lacking data of follow-up.

X. The inventor cooperated with physicians of 302 Hospital of Anshun in his effort to treat 120 patients with headache with the chips.

1. About clinical data:

Of the 120 patients, 39 were men and 81 were women. The youngest patient was 20 years old and the oldest was 70. The shortest disease course was 5 hours and the longest was 20 years.

2. About treatment:

2.1 Master Acupuncture Points were Fengchi, Baihui, matched with other Acupuncture Points according to syndrome differentiation. The patients were clinically classified as: (1) Affection due to external wind: headache occurred upon encountering wind and pain was striking. They were matched with Fengfu, Lieque, Waiguan, Hegu. (2) Liver-Yang: pain on one side, may be involving top of head. They were matched with Sishencong, Taichong and Shuiquan. (3) Stasis of blood: refractory and pricking pain. They were matched with SanYinjiao and Ashixue.

2.2 Procedures: Dip a cotton stick into surface liquid and moisten the contact area on the skin, apply the chip onto the Acupuncture Points and immobilize it with poromeric adhesive tape. Retain the chip on Acupuncture Points for one hour each session of therapy. Once daily and ten sessions make up one therapeutic course. A two-day interval is needed before administering next therapy. Analyze effectiveness after one therapeutic course.

3. Criteria for determining effectiveness:

3.1 Cure: pain disappears utterly and does not relapse within half a year; obvious effectiveness: pain obviously become alleviated and less frequent; some certain effectiveness: pain become alleviated and less frequent; no effect: pain remains unchanged.

3.2 Outcome of therapy: Among 120 patients, 96 patients were treated, accounting for 80%; 18 patients showed obvious effectiveness, accounting for 15%; 6 patients showed some certain effectiveness, accounting for 5%. The effectiveness rate was 100%.

XI. The inventor cooperated with physicians of No. 1 Hospital for Traditional Chinese Medicine of Changde City in his effort to treat 50 patients with gastric or duodenal ulcer with the chip. The therapeutic effect is satisfactory.

1. About patients and treatment:

1.1 Selection of patients: All 80 patients met criteria for gastric or duodenal ulcer. They were randomized into two groups. The treatment group had 50 patients. 35 were men and 15 were women, the ages were between 24-62 and an average of 35.5±11.3. Disease courses were between 0.5-20 years with an average of 6.4±2.8. 19 patients were suffering gastric ulcer, 26 patients were suffering duodenal ulcer, 5 patients were suffering compound ulcer, 44 patients had negative occult blood in stool, 4 patients had weak positive result and 2 had positive result. The control group had 30 patients. 18 were men and 12 were women, the ages were between 20-68 and an average of 34.4±12.4. Disease courses were between 4 months-18 years with and average of 6.5±3.0. 10 patients were suffering gastric ulcer, 13 patients were suffering duodenal ulcer, 7 patients were suffering compound ulcer, 25 patients had negative occult blood in stool, 3 patients had weak positive result and 2 had positive result. Differences between the two groups were tested non-significant using X2 (P>0.05), being comparable.

1.2 About treatment:

For the treatment group: first group: Zusanli, Neiguan, Gongsun; second group: Zhongwan, Pishu, Weishu. Add liangQiu in case of stomach pain; add upper and lower Zhongwan in case of cold in stomach; add Tianshu in case of flatulence; add Taichong in case of sour regurgitation; add Zhigou in case of constipation; add Shenmen in case of insomnia; add Qihai in case of fatigue. Alternate the two grouped Acupuncture Points once daily.

Dip a cotton stick into surface liquid and moisten the contact area on the skin, apply the chip onto the Acupuncture Points and immobilize it with poromeric adhesive tape. Retain the chip on Acupuncture Points for one hour each session of therapy. Once daily and ten sessions make up one therapeutic course and keep the treatment for 2 months posterior to therapy with the chips. For control group, Acupuncture Points were taken the same as that of treatment group except for using supplementing or dispelling maneuver. For bleeding ulcers (mild), some medications could be used.

1.3 Parameters for observation: ulcer lesion (gastroscopy), and some symptoms (abdominal pain, sour regurgitation).

1.4 Criteria for determining effectiveness in accordance with Standard for Determining Effectiveness over Diseases Treated with Traditional Chinese Medicine issued in 1994 by State Administration of Traditional Chinese Medicine of PR China.

Clinically treated: ulcer lesion heals found by gastroscopy, symptoms disappear; obvious effectiveness: ulcer lesion shrink or become scared found by gastroscopy, symptoms disappear or become alleviated; alleviated: lesion does not shrink, but congestion and edema in membrane of stomach become alleviated, and symptoms become alleviated; no effect: ulcer remains unchanged (lesion and symptoms remain unchanged).

2. Result: For results, see Tables 1 and 2.

TABLE 1

Comparison between two groups over effectiveness

| main symptoms | Number of patient | Cure | Obvious effectiveness | Alleviated | No effect | General effectiveness rate (%) |
|---|---|---|---|---|---|---|
| Treatment group | 50 | 14 | 11 | 21 | 4 | 92.01 |
| Control group | 30 | 6 | 6 | 13 | 5 | 83.3 |

TABLE 2

Comparison between two groups over time consuming upon getting effectiveness

| Group | Number of patient | Therapeutic course | | | |
|---|---|---|---|---|---|
| | | 6 | 7 | 8 | 9 |
| Treatment group | 14 | 2 | 5 | 5 | 2 |
| Control group | 6 | 0 | 0 | 2 | 4 |

XII. The inventor cooperated with physicians of People's Hospital of Jinshi County in his effort to treat vascular headache with the chips.

1. About clinical data:

Among the 120 patients, 35 were men and 85 were women. The youngest was 18 years old and the oldest was 76. The longest therapeutic course lasted 10 years and the shortest course was one day.

2. About treatment:

Acupuncture Points were classified into four groups. The first group: Yintang, Yongquan, Hegu; the second group: Yintang, Fengchi, Zhongwan; the third group: Neiguan, Yifeng, TaiYang. For headache in full head, add Acupuncture Points along hairline; the fourth group: Fengchi, Neiguan, TaiYang, Shuaigu.

Procedures: Dip a cotton stick into surface liquid and moisten the contact area on the skin, apply the chip onto the Acupuncture Points and immobilize it with poromeric adhesive tape. Retain the chip on Acupuncture Points for one hour each session of therapy. Once daily and ten days make up one therapeutic course. A two-day interval is needed before every two sessions and evaluating therapeutic effect after two therapeutic courses.

3. Observations of effectiveness and results:

Criteria for determining effectiveness

Clinically treated: pain disappear and normal life restored, pain does not relapse within half a year follows; obvious effectiveness: pain disappear and normal life restored, but relapses within half a year follows; some certain effectiveness: pain becomes alleviated, but becomes deteriorated in case of tiredness and fretfulness, relapses sometimes: no effect: pain remains unchanged.

4. Outcome of therapy 120 patients were treated; 20 patients showed obvious effectiveness; 20 patients showed some certain effectiveness; 12 patients showed no effect 3 patients. General effectiveness rate was as high as 97.5%.

XIII. The inventor cooperated with physician Duan Changjiu in his effort to treat 48 patients with bronchial asthma with the chips.

1. About clinical data:

Among the 48 patients, 20 were men and 28 were women. The youngest was 6 years old and the oldest was 65. The longest therapeutic course lasted 27 years and the shortest course was 6 months. 36 patients were due to phlegm-hot, 12 were due to wind-cold.

This disease was mostly due to wax of evil and wane of genuine, manifesting excess of viscera upon onset, either displaying cold or hot feature. Symptoms can be short breath and choked chest, wheeze, loud speaking and powerful pulse. For those who are displaying cold features, their sputum was cold and thin complicated by coldness signs; for those who are displaying hot features, they had more expiration and less inspiration, exacerbated by motion, short breath, fatigue, gloomy complexion and weak pulse. Protracted disease course may hurt spleen and kidney and be complicated with deficiency in both spleen and kidney.

2. About treatment:

Acupuncture Points: Neiguan, Tiantu, Dingchuan, Shanzhong, Feishu, Chize, Zusanli, Yuji, Yezui, Lieque. Alternately use 4-5 Acupuncture Points.

Treatment: Dip a cotton stick into surface liquid and moisten the contact area on the skin, apply the chip onto the Acupuncture Points and immobilize it with poromeric adhesive tape. Retain the chip on Acupuncture Points for one hour each session of therapy. Once daily and ten sessions make up one therapeutic course.

3. Effectiveness of treatment:

3.1 Criteria for determining effectiveness

Obvious effectiveness: symptoms are removed without relapse within half a year, or occasionally relapse but very slightly, can be relived without anti-asthma medications.

Alleviated: symptoms obviously become alleviated, can restore normal life although symptoms may occur here and there, and anti-asthma medications are reduced dramatically.

No effect: symptoms remain unchanged after three therapeutic courses.

3. 2 Outcome of therapy:

15 patients showed obvious effectiveness, accounting for 315; 30 patients showed some certain effectiveness, accounting for 63%; 3 patients showed no effect, accounting for 6%; general effectiveness rate was 94%.

TABLE

Effectiveness over types of asthma treated with acupuncture

| Main symptoms | Number of patient | Obvious effectiveness | Alleviated | No effect | General effectiveness rate (%) |
|---|---|---|---|---|---|
| Treatment group | 36 | 12 (33) | 23 (64) | 1 (3) | 97 |
| Control group | 12 | 3 (25) | 7 (58) | 2 (17) | 83 |

Compared to other procedures of CAM (Complementary and alternative medicines), this chip is more effective and enjoys additional advantages as below:

3.2.1 Free from using needle and medications, free from any side or toxic effect. It is superior to invasive procedures, and meets requirements for non-deleteriousness and environment-friendliness.

3.2.2 Free from using electricity and mechanic parts, free from damage and maintenance. It is better than electricity-mechanic peers.

3.2.3 Easily use very accessible for self-rehabilitation and household use. Free from maneuver of practitioner, being exempted from poor effect due to inappropriate practice.

3.2.4 Economical and cheap: This chip can be used personally and can endure repeated uses as many as tens of thousand times, costing only several cents each session of therapy.

Example I

The Method and Processing of Manufacturing and Using the Health Recovery Chips

1. The method and processing of manufacturing the chips 1.1 The row material for making the chip consists of (by weight): Polar mineral tourmaline powder 35%; Infrared material powder 30% ($AL_2O_3$ 20% and MgO 10%); Pliable magnetic material powder (FeO) 20%; The photo-catalytic material nanometer powder 3% (ZnO 2% and $TiO_2$ 1%); Composite salt of rare-earth $LaPO_4$ 3%; Calcium oxide 5%; Adhesive material 2% (Stearic Acid 1% and Flex oil 1%); an Inclusion compound 2% (Liquid Paraffin Wax 1% and Colophon 1%).

1.2 The polar mineral Tourmaline is routinely smashed into fine powder proceeding to either placing into the high-energy ball mill to grind or be pulverized through the airflow millstone 60 hours. Either process will results in very small particles with crystalline grain diameter between 50-1000 nanometers. The thermal treatment will then be applied to tourmaline material with a range of temperature of about 900° C., which is about 2 hours. The same procedures also apply to the Infrared material.

1.3 Putting above eight listed of material into a grinding and blending machine to grind and blend for 1 hour. The blended material is placed into mould plate according to predefined shapes. The pressure is 30 Mpa. After pressing, the formed chip is taken out of the mould plate and sintered by thermal treatment. The thermal treatment is performed at temperature between 900° C. for 2 hours. Then, the chip is left at room temperature for self-cooling 48 hours and the chips are finalized. The finished chips are the diameter=25 mm and the thickness=4 mm.

2. Manufacture superficial fluid: submerging 2 of the finalized chips into 200 ml clean water for one hour, and then bottling the water.

3. Manufacture the awl: the mountain jade ore from Liaoning of China is cut and polished into awl shape. The awl has a base with a diameter of 0.6-0.8 cm, length of 7 cm, and a dull tip.

4. Manufacturing gains the effect membrane: The LLD-PEC low density string shaped polythene is mixed with corn oil to make a 0.18 mm thickness stretching membrane. It is rolled and cut into 5 cm in width.

5. Basic using method: Putting the superficial fluid between chip and the point you apply, and then putting the chips on the points you selected. Using the effect membrane cover to fixed. After 10 minutes, there are chili, sting, pain and hot sensations and redness on the point. The sensations will automatically reduce after 40 minutes. The whole treatment is one hour. After finishing one session, the chips are removed from the body; the sensations and redness will disappear in 30 minutes without any damage of the skin. One course of treatment is 10 sessions once a day, even the symptom of the diseases will mitigate; it is a recommendation to keep the treatment for 1-3 courses.

Example II

The Method and Processing of Manufacturing and Using the Health Recovery Chips

1. The method and processing of manufacturing the chips 1.1 The row material for making the chip consists of (by weight): Polar mineral tourmaline powder 30%; Infrared material powder $AL_2O_3$ 20%; Pliable magnetic material powder (FeO) 30%; The photo-catalytic material (SnO 1% and ZnO 1%); Composite oxide of rare-earth $CeO_2$ 3%; Calcium oxide 10%; Adhesive material 3% (Polyvinyl chloride 2% and Pine resin 1%); an Inclusion compound 2% (Methyl cellulose 1.5% and Colophon 0.5%).

1.2 The polar mineral Tourmaline and Infrared material are routinely smashed into fine powder proceeding to either placing into the high-energy ball mill to grind or be pulverized through the airflow millstone 60 hours. Either process will results in very small particles with crystalline grain diameter between 50-1000 nanometers. The thermal treatment will then be applied to tourmaline material with a range of temperature of about 900° C., which is about 2 hours.

1.3 Putting above eight listed of material into a grinding and blending machine to grind and blend for 1 hour. The blended material is placed into mould plate according to predefined shapes. The pressure is 30 Mpa. After pressing, the formed chip is taken out of the mould plate and sintered by thermal treatment. The thermal treatment is performed at temperature between 900° C. for 2 hours. Then, the chip is left at room temperature for self-cooling 48 hours and the chips are finalized. The finished chips are the diameter=25 mm and the thickness=4 mm.

2. Manufacture superficial fluid: submerging 2 of the finalized chips into 200 ml clean water for one hour, and then bottling the water.

3. Manufacture the mountain jade ore: the mountain jade ore from Liaoning of China is cut and polished into awl shape. The awl has a base with a diameter of 0.6-0.8 cm, length of 7 cm, and a dull tip.

4. Manufacturing gains the effect membrane: The LLD-PEC low density string shaped polythene is mixed with corn oil to make a 0.18 mm thickness stretching membrane. It is rolled and cut into 5 cm in width.

5. Basic using method: Putting the superficial fluid between chip and the point you apply, and then putting the chips on the points you selected. Using the effect membrane cover to fixed. After 10 minutes, there are chili, sting, pain and hot sensations and redness on the point. The sensations will automatically reduce after 40 minutes. The whole treatment is one hour. After finishing one session, the chips are removed from the body; the sensations and redness will disappear in 30 minutes without any damage of the skin. One course of treatment is 10 sessions once a day, even the symptom of the diseases will mitigate; it is a recommendation to keep the treatment for 1-3 courses.

The invention claimed is:

1. An acupuncture replacement device in the form of a solid chip comprising a mixture of the following:
    (a) 20 to 40% by weight of a polar tourmaline powder selected from the group consisting of iron tourmaline, magnesium tourmaline, iron and magnesium tourmaline, and lithium tourmaline, said tourmaline powder having a crystalline grain diameter of 50 to 1000 nanometers and which has been thermally treated with a temperature of from 500 to 1000° C.;
    (b) 30 to 50% by weight of an infrared refractive material selected from the group consisting of $Al_2O_3$, and MgO;

(c) 5 to 10% by weight of a pliable magnetic material selected from the group consisting of FeO, and $Fe_2O_3$;
(d) 1 to 5% by weight of a photo-catalytic material having a grain diameter of from 50 to 1000 nanometers and selected from the group consisting of $TiO_2$, ZnO, and SnO;
(e) 1 to 5% by weight of a composite salt selected from the group consisting of $La_2O_3$, $Nd_2O_3$, $LaPO_4$, $Ce(NO_3)_3$, and $La(NO_3)$;
(f) 5 to 10% by weight of CaO;
(g) 2 to 5% by weight of an adhesive material selected from the group consisting of stearic acid, pine resin, flax oil, and castor oil; and
(h) 1 to 5% by weight of an inclusion compound material consisting of methyl cellulose.

2. The acupuncture replacement device according to claim 1 wherein said infrared refractive material has a crystalline grain diameter of between 50 to 1000 nanometers which has been thermally treated with a temperature of from 500 to 1000° C.

\* \* \* \* \*